United States Patent [19]
Dziemian et al.

[11] 3,944,671
[45] Mar. 16, 1976

[54] TREATMENT OF ADRENAL MALFUNCTION

[75] Inventors: Robert Dziemian, Cedar Knolls; Neville Finch, West Orange, both of N.J.

[73] Assignee: Ciba-Geigy Corporation, Ardsley, N.Y.

[22] Filed: Sept. 12, 1973

[21] Appl. No.: 396,969

[52] U.S. Cl. .................................................. 424/267
[51] Int. Cl.² ........................................ A61K 31/445
[58] Field of Search ....................................... 424/267

[56] References Cited
UNITED STATES PATENTS
3,595,960   7/1971   Gaunt ............................ 424/267

OTHER PUBLICATIONS

The Merck Manual, 12 ed., 1972, Merck & Co. Inc., Rahway, N.J., pp. 1168–1174.

*Primary Examiner*—Stanley J. Friedman
*Attorney, Agent, or Firm*—Joseph G. Kolodny; Theodore O. Groeger; John J. Maitner

[57] ABSTRACT

Dextrorotatory α-(4-aminophenyl)-α-lower alkyl-glutarimides or salts thereof normalize the secretion of malfunctioning adrenal glands.

10 Claims, No Drawings

TREATMENT OF ADRENAL MALFUNCTION

BACKGROUND OF THE INVENTION

According to U.S. Pat. No. 2,848,455 recemic α-(4-aminophenyl)-α-lower alkylglutarimides, acid addition salts or lower alkanoyl derivatives thereof "exhibit anticonvulsive activity". The α-ethyl derivative, i.e. aminoglutethimide, its hydrochloride or phosphate, has been used in the form of injectable solutions or 125 and 250 mg tablets, as an anticonvulsant which, alone, or particularly as an adjunct, controls seizures in most forms of epilepsy, even in cases refractory to other therapeutic agents.

Furthermore, it has been shown that aminoglutethimide inhibits at high dosage levels the secretion of adrenal cortical hormones in both animals and man. Thus, according to U.S. Pat. No. 3,595,960 a method of treating hypertensives with reduced renin blood levels and normal or reduced mineralocorticoid secretion rate is disclosed, which consists in the administering to a host suffering from said hypertension about 8 to 15 mg/kg/day of a recemic α-(4-aminophenyl)-α-lower alkylglutarimide, or its therapeutically acceptable acid addition salt or lower alkhanoyl derivative.

Suprisingly it has been found that the major known biological activities of said racemic products reside in the dextrorotatory antipodes, especially the inhibitory effects on the adrenal gland.

SUMMARY OF THE INVENTION

The present invention concerns and has for its object the provision of a new pharmaceutical composition comprising a pharmacologically effective amount of the dextrorotatory antipode of an α-(4-aminophenyl)-α-lower alkylglutarimide, or its lower alkanoyl derivative corresponding to Formula I

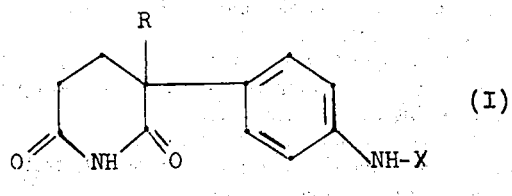

wherein R (at the asymmetric carbon or α-position) is lower alkyl and X is hydrogen or lower alkanoyl, or a therapeutically acceptable acid addition salt thereof, and a pharmaceutical excipient; as well as a new method of treating a host suffering from malfunctioning adrenal glands with said dextrorotatory compounds of Formula I, or salts thereof, advantageously in the form of orally applicable pharmaceutical compositions, and preferably in a dosage range higher than the 8 to 15 mg/kg/day claimed in U.S. Pat. No. 3,595,960, which amounts to 4 to 7.5 mg/kg/day of the dextrorotatory ingredients.

DESCRIPTION OF THE PREFERRED EMBODIMENTS

The active ingredients of the compositions claimed herein are prepared from the racemic products described in U.S. Pat. No. 2,848,455 by conventional separation methods. Thus, for example, the free bases are salified or acylated with optically active acids, such as carboxylic or sulfonic acids, the diastereomeric salts or amides are separated, e.g. by the fractional crystallization, of d- or l-tartrates, -maleates, -mandelates, -N-acetylphenylalaninates, -quinates, -6,6'-dinitrodiphenates or-camphorsulfonates and, if desired, resulting salts or amides are converted into the free antipodes by alkaline hydrolysis, e.g. with the use of aqeous alkali metal hydroxides or carbonates.

Said antipodes can be used in the free form or in the form of therapeutically acceptable acid addition salts thereof. Preferred salts are those of inorganic acids, e.g. hydrochloric, hydrobromic, sulfuric, nitric, perchloric or expecially phosphoric acid, but also those of organic acids, such as carboxylic or sulfonic acids, e.g. formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicylic, aminosalicylic, pamoic, nicotinic, methanesulfonic, ethanesulfonic, hydroxyethanesulfonic, ethylenesulfonic, benzenesulfonic, halogenbenzenesulfonic, toluenesulfonic, naphthalenesulfonic or sulfanilic acid; methionine, tryptophan, lysine or arginine.

The efficacy of the compositions according to the invention is demonstrable in animal tests, using advantageously mammals, such as mice or rats, as test objects. Thus, for example, the effect on the adrenal secretion is determined according to Chart, Progr. in Endocrinol. ICS 184 Excerpta Medica, Amsterdam (1968) and the adrenal vein corticosterone-levels are estimated by fluorometry according to Van der Vies et al, Acta Endocrinol. 34, 513 (1960). According to the results obtained with an aqueous d-aminoglutethimide d-tartrate hemihydrate solution (an illustrative composition of the invention), when injected into the tail vein of rats at a dose of 5 mg/kg/day, caused a greater reduction of corticosterone blood-levels than 10 mg/kg/day of the corresponding aqueous solution of racemic aminoglutethimide phosphate, and the levorotatory tartrate antipode did not cause a significant reduction of the corticosterone secretion rate. Similar results can be observed in rats after oral administration of said solution, or starchy suspensions, at doses between about 5 and 120 mg/kg/day, at which latter high dosage level also some depression, ataxia, loss or righting reflex or startle response and loss in grip and climbing occurs. Accordingly, the compositions of the invention are preferably useful in the treatment of adrenal hyperfunction, especially in cases not amenable for surgery.

The new method for treating a host suffering from malfunctioning, more particularly oversecreting, adrenal glands consists in administering to him enterally or parenterally, e.g. orally or intravenously, a pharmacologically effective amount of said new compositions, preferably at a dosage level between about 8 and 80 mg/kg/day, advantageously between about 10 and 30 mg/kg/day, of said dextrorotatory compounds of Formula I, or their salts, either in a single, or preferably in multiple dosage units, e.g. between about 450 and about 1,000 mg per oral unit dosage form.

Preferred are tablets and gelatin capsules comprising the active ingredient together with a) diluents, e.g. lactose, dextrose, sucrose, mannitol, sorbitol, cellulose and/or glycine, b) lubricants, e.g. silica, talcum, stearic acid, its magnesium or calcium salt and/or polyethyleneglycol, for tablets also c) binders, e.g. magnesium aluminum silicate, starch paste, gelatin, tragacanth, methylcellulose, sodium carboxymethylcellulose and/or polyvinylpyrrolidone, if desired, d) disintegrants, e.g. starches, agar, alginic acid or its sodium salt, enzymes of the binders or effervescent mixtures and/or e) adsorbents, colorants, flavors and sweeteners. Injectable compositions are preferably aqueous isotonic solutions or suspensions, and suppositories are advantageously fatty emulsions or suspensions. They may be sterilized and/or contain adjuvants, such as preserving, stabilizing, wetting or emulsifying agents, solution promoters, salts for regulating the osmotic pressure and/or buffers. Said pharmaceutical compositions may also contain other therapeutically valuable substances. They are prepared according to conventional mixing, granulating or coating methods respectively, and contain about 10 to 90%, preferably about 20 to 80%, of the active ingredient by weight.

The following examples are intended to illustrate the invention and are not to be construed as being limitations thereon.

EXAMPLE 1

The stirred mixture of 709 g of d,l-aminoglutethimide, 460 g of d-tartaric acid and 20 lt of methanol is heated until dissolution occurs and allowed to slowly cool to room temperature. The precipitate formed is filtered off and recrystallized five times from methanol, to yield the d-aminoglutethimide d-tartrate hemihydrate, melting at 135° to 145°, $[\alpha]_D^{25} = +79°$ (methanol).

7.65 g thereof are dissolved in 75 ml of water and the solution is neutralized with an aqueous solution of 2.1 g of sodium carbonate. The precipitate is collected, washed with water and dried, to yield the d-aminoglutethimide melting at 114–115°, $[\alpha]_D^{25} = +163.1°$ (methanol).

EXAMPLE 2

All the methanolic mother liquors obtained according to Example 1 are evaporated, to yield a residue of 387 g. It is dissolved in 2.5 lt of methanol, the solution neutralized with 105 g of sodium carbonate in 450 ml of water, the mixture washed with methylene chloride and the precipitate collected. It is combined with 100 g of d,l-aminoglutethimide, dissolved in 9 lt of hot methanol containing 202 g of l-tartaric acid and the solution allowed to cool slowly to room temperature. The precipitate formed is filtered off and recrystallized four times from methanol, to yield the l-aminoglutethimide l-tartrate hemihydrate, $[\alpha]_D^{25} = -80°$ (methanol).

It is cnverted into the free l-base as shown in Example 1, m.p. 114–115°, $[\alpha]_D^{25} = -163°$ (methanol). Accordingly, the physical data obtained confirm the optical purity of the valuable dextrorotatory compounds of Example 1.

EXAMPLE 3

To the solution of 2.32 g of d-aminoglutethimide in 6 ml of hot ethanol, 1.4 g of 85% phosphoric acid are added while stirring and the mixture allowed to cool to room temperature. The precipitate formed is filtered off, washed with ethanol and dried, to yield the d-aminoglutethimide monophosphate hemiethanolate melting at 113–116°, $[\alpha]_D^{25} = +108°$ (methanol).

Analogously the l-aminoglutethimide monophosphate hemiethanolate is prepared, m.p. 113–116°, $[\alpha]_D^{25} = -107°$ (methanol).

EXAMPLE 4

In order to establish the absolute configuration of the compounds of the invention, the compound of Example 2 was converted into the l-glutethimide ($\alpha$-ethyl-$\alpha$-phenylglutarimide), and the latter compared with the $\alpha$-ethyl-$\alpha$-phenylsuccinimide, the absolute configuration of which has been established by Knabe et al, Arch. Pharmazie 305, 849 (1972), assuming that said glutarimides and succinimides will have the same chirooptical behavior if they contain the same chirality.

To the solution of 1.16 g of l-aminoglutethimide in 1 ml of concentrated hydrochloric acid and 6.2 ml of water, that of 0.4 g of sodium nitrite in 0.8 ml of water is added during 20 minutes while stirring at 10°. Stirring is continued for another 20 minutes and the mixture poured into the ice-cold mixture of 3.1 ml of 50% hypophosphorous acid and 2.1 ml of water. It is allowed to stand overnight in the refrigerator, extracted with diethyl ether and the extract washed with 5% hydrochloric acid, 5% aqueous sodium carbonate, water and saturated aqueous sodium chloride. It is dried, evaporated, the residue chromatographed on silica gel and the column eluted with chloroform-ethyl acetate (4:1). The early fractions are evaporated and the residue recrystallized from cyclohexane, to yield the l-glutethimide melting at 97°–98°, $[\alpha]_D^{25} = -183.7°$ (methanol).

Due to the fact that the CD-curve of said l-glutethimide is nearly identical with that of the known S-$\alpha$-ethyl-$\alpha$-phenylsuccinimide, the compounds of Example 2 are the S-l-aminoglutethimide or its salt, and those of Examples 1 and 3 are the R-d-aminoglutethimide or its salts.

We claim:

1. A pharmaceutical composition for reducing adrenal hyperfunction, comprising an adrenal secretion reducing amount of the dextrorotatory antipode of an $\alpha$-(4-aminophenyl)-$\alpha$-lower alkylglutarimide or a therapeutically acceptable acid addition salt thereof, and a pharmaceutical excipient.

2. A composition as claimed in claim 1, wherein the antipode is d-aminoglutethimide or a therapeutically acceptable acid addition salt thereof.

3. A composition as claimed in claim 2, wherein the antipode is the d-aminoglutethimide d-tartrate.

4. A composition as claimed in claim 2, wherein the antipode is the d-aminoglutethimide monophosphate.

5. A composition as claimed in claim 1, wherein the antipode content is about 10 to 90% by weight.

6. A composition as claimed in claim 5, wherein the antipode content is about 20 to 80% by weight.

7. A composition as claimed in claim 1, containing between about 450 and about 1,000 mg of the antipode per oral unit dosage form.

8. A method of treating a mammal suffering from malfunctioning adrenal glands, which consists in administering to him enterally or parenterally an adrenal secretion reducing amount of the composition claimed in claim 1.

9. A method as claimed in claim 8, wherein the effective amount of the antipode is between about 8 and 80 mg per kilogram body weight per day of treatment.

10. A method as claimed in claim 8, wherein the effective amount of the antipode is between about 10 and 30 mg per kilogram body weight per day of treatment.

* * * * *